United States Patent [19]

Grisar

[11] Patent Number: 4,638,794
[45] Date of Patent: Jan. 27, 1987

[54] JOINT CUFF

[76] Inventor: Gunter Grisar, Am Suedhang 3B, D-6301 Wettenberg 3, Fed. Rep. of Germany

[21] Appl. No.: 702,512

[22] Filed: Feb. 19, 1985

[30] Foreign Application Priority Data

Feb. 23, 1984 [DE] Fed. Rep. of Germany ... 8405572[U]
Sep. 29, 1984 [DE] Fed. Rep. of Germany ....... 3435955

[51] Int. Cl.[4] .......................... A61F 5/37; A61F 5/14
[52] U.S. Cl. ................................ 128/80 H; 128/595
[58] Field of Search .............................. 128/80 H, 595

[56] References Cited

U.S. PATENT DOCUMENTS

| | | | |
|---|---|---|---|
| 1,465,233 | 8/1923 | Posner | 128/166 |
| 2,450,862 | 10/1948 | Wilkinson | 128/80 H |
| 3,545,447 | 12/1970 | Silverman | 128/595 |
| 3,584,622 | 6/1971 | Domenico | 128/166 |
| 3,674,023 | 7/1972 | Mann | 128/166 |
| 3,814,088 | 6/1974 | Raymond | 128/80 H |
| 3,905,376 | 9/1975 | Johnson et al. | 128/559 |
| 4,103,897 | 8/1978 | Ostyn | 128/80 H |
| 4,280,489 | 7/1981 | Johnson, Jr. | 128/80 H |
| 4,287,920 | 9/1981 | Johnson, Jr. | 141/85 |
| 4,411,077 | 10/1983 | Slavitt | 128/80 H |
| 4,446,856 | 5/1984 | Jordan | 128/80 H |
| 4,510,927 | 4/1985 | Peters | 128/80 H |

FOREIGN PATENT DOCUMENTS 209486 11/1959 Austria .
1740508 11/1956 Fed. Rep. of Germany .

Primary Examiner—Edgar S. Burr
Assistant Examiner—Tonya Eckstine
Attorney, Agent, or Firm—Flynn, Thiel, Boutell & Tanis

[57] ABSTRACT

A joint cuff is provided for supporting and guiding an ankle joint and for preventing lateral twisting while assuring movement perpendicular to the joint axis. The joint cuff includes two side portions which laterally grip the joint and are connected with one another by a bottom portion. The joint cuff has, in an open condition, a somewhat V-shaped form. It includes a strip of a low-temperature plastic, and the two side portions are dimensioned so that the tibia remains free of the cuff at its front and back side, while the joint is gripped laterally. To adjust the cuff to a particular individual, the cuff is warmed up and is fitted to the shape of the ankle joint directly on the foot of the patient.

8 Claims, 3 Drawing Figures

JOINT CUFF

FIELD OF THE INVENTION

This invention relates to a joint cuff and, in particular, to a joint cuff for supporting and guiding the ankle joint.

BACKGROUND OF THE INVENTION

For persons who have suffered an ankle joint distortion, who have a loose ligament in the upper or lower ankle joint, who have had surgery because of torn ligaments, or who have an ankle joint particularly susceptible to injuries, for example football players, handball players, basketball players and volleyball players, supporting and guiding of the ankle joint by a joint cuff is necessary.

Joint cuffs are known, for example for the support of the ankle joint, which consist of a rubber stocking which is formed anatomically and is compression intensive, and in this manner assures a close fit. However, the disadvantage of such a stocking is that it does not offer any protection against distortions and does not protect against force effects of even the smallest degree.

It is further known to reinforce such a rubber stocking with lateral spiral springs which lie above the ankle joint, in order to achieve a stability increase with respect to the rubber stocking. Of course, the stability achieved is insignificant, while the other disadvantages continue to exist.

Moreover, ankle lacing bandages are known which are made of an artificial leather with laterally cushioned rails and instep bone lacing. In the region of the ankle joint, elastic rails are provided which provide reinforcement. Of course, these elastic members cannot be adjusted to the ankle joint of each particular individual, and thus even a strong lacing does not bring sufficient stability.

Furthermore, sports shoes are known in which reinforcing bars are provided which are pulled up laterally over the ankle joint and are supposed to prevent twisting during sports. These reinforcing bars consist of an elastic material, so that they can adapt to the shape of the ankle bone of each individual. The stability gain is, however, only relatively small, since the adjusting of the reinforcing bars to the shape of the foot is rather imperfect. Furthermore, there exists the disadvantage that a special shoe is needed.

Furthermore, tape bandages are known, which have the disadvantage that they can be used only once and cannot be applied over scrape wounds.

U.S. Pat. No. 4,280,489 discloses an ankle joint cuff in which laterally of and under the foot a U-shaped strip of a thermoplastic is provided, on the inner side of which is an inflatable air hose which extends at least the entire width of the U-shaped plastic part. The U-shaped plastic part serves as an abutment for the inflatable hose which, when the cuff is worn, is located between the ankle joint and the abutment. The air hose is inflated and is supposed to apply pressure laterally onto the joint, so that the joint is supported laterally. The disadvantage of this known ankle joint cuff, however, is that the air pressure cannot be increased sufficiently so that lateral movement of the ankle joint is not possible, because otherwise the pressure applied onto the foot would be unbearably high. Furthermore, it has been shown in practice that the portion which extends under the foot is annoying during walking, so much so that it has in fact been replaced in practice with a band, which has resulted in a reduction of the stability of the joint cuff. As to the efficiency of this joint cuff, it does not bring any greater safety than the previously discussed joint cuffs.

A basic purpose of the invention is to provide a joint cuff of the above-mentioned type which prevents with certainty a twisting of, for example, the ankle joint during maximum athletic effort and thus satisfactorily supports the joint, which can be permanently fitted in a simple manner to the individual joint of the person to be treated, and which does not limit the capability of movement in the upper and lower ankle joint, permits rotation movements, and at the same time serves as a bone protector.

SUMMARY OF THE INVENTION

This purpose is attained by providing a joint cuff, for example for the ankle joint, which includes two side portions which are placed laterally over the ankle joint. The two side portions are connected with one another by a bottom portion which extends under the foot. In its open condition, the joint cuff is somewhat V-shaped, and the width of the bottom portion is slightly less than the width of each side portion. The width of the side portions is chosen so that it does not limit the capability of movement in the upper and lower ankle joint. The joint cuff includes a low-temperature thermoplastic, preferably a thermoplastic which can be deformed at temperatures which are as low as possible. Thermoplastics are known which can be deformed starting at only 55° C. For adjusting the inventive joint cuff, it is for example placed into a waterbath at 60°-70° C. and is thus heated up to this temperature. The cuff is subsequently pressed onto the foot and ankle joint and adapts to the shape of the ankle joint and foot, whereby the low-temperature thermoplastic receives a satisfactory complementary image of the individual ankle joint, or any other joint, as it cools. Thus, each ankle joint cuff is precisely fitted to the unique shape of the foot of the person wearing it. For securing the ankle joint cuff, the two side portions can be fixed at their upper ends, either by a bandage encircling the tibia or by an adhesive band. Decisive for the high stiffness and the secure hold of the ankle joint cuff is thus the fact that the two side portions are connected with one another in a manner resistant to bending by the bottom portion and the fact that a form-fitting engagement with the contour of the foot and joint exists, so that even when a large force acts onto the ankle joint, as can occur during competitive sports, lateral mobility of the foot relative to the cuff, and thus twisting, is prevented with certainty.

For comfortable wearing of the ankle joint cuff, it can include on the inner side of the thermoplastic material a cushion layer, for example a foam layer. The cuff advantageously includes a cover made of leather, artificial leather or fabric in order to give it a more attractive appearance, and also to cover the cushion layer.

BRIEF DESCRIPTION OF THE DRAWINGS

One embodiment of the invention will be described in greater detail hereinafter in connection with the drawing, in which.

DETAILED DESCRIPTION OF THE DRAWINGS

Figure 2:
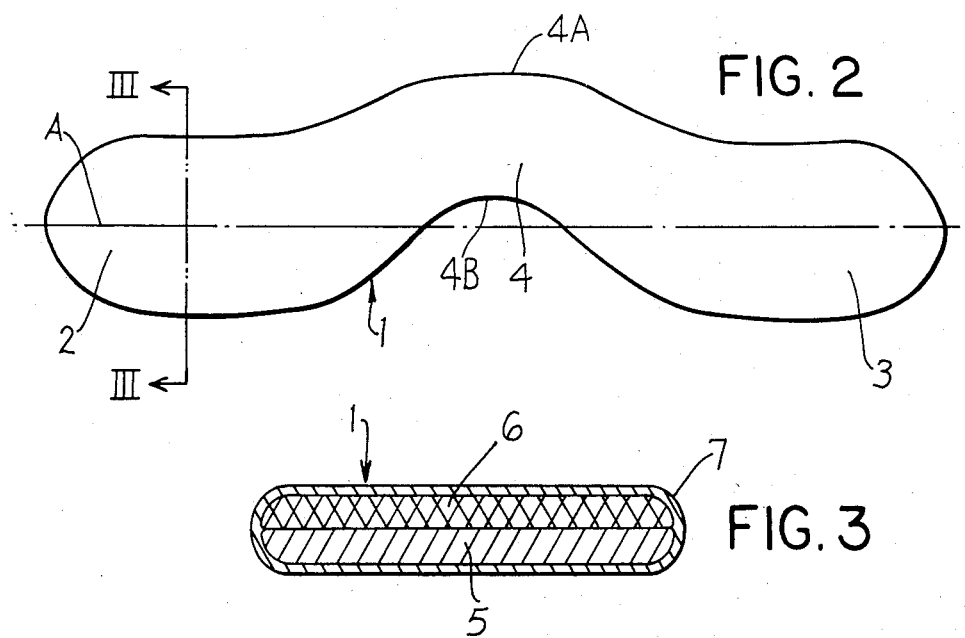
FIG. 2 is a top view of the joint cuff in an opened condition.
Figure 3:
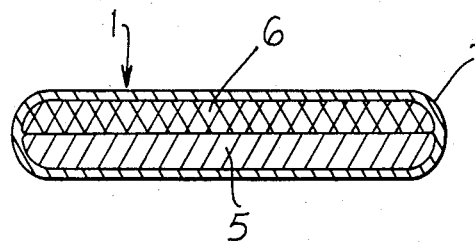
FIG. 3 is a sectional view taken along the line III—III in FIG. 2.

The joint cuff which is illustrated in the figures is illustrated in the opened condition in FIG. 2 and has a somewhat V-shaped form. The cuff has two elongated and longitudinally aligned side or end portions 2 and 3 aligned along a central longitudinal axis A, and the portions 2 and 3 each have a slightly greater width than a center or bottom portion 4 of the cuff which connects the two portions 2 and 3 with one another. Both lateral edges 4A and 4B of the bottom portion 4 define an obtuse angle, the opening angle for both edges being in the same direction so that the entirety of the bottom portion extends to one lateral side of the longitudinal axis A as shown in FIG. 2. The ankle joint cuff includes a one-piece strip 5 of a low-temperature thermoplastic, for example a thermoplastic material which can be plastically deformed at or above 55° C. and, after cooling off, maintains the shape imparted to it while heated. This plastic strip 5 has on one side a cushion layer 6 which rests on the human joint, and thus makes wearing of the cuff 1 easier. The cushion layer 6 can advantageously be made of a foam material. The strip 5 and cushion layer 6 are surrounded by a protective sleeve or cover 7, which can for example be made of leather, artificial leather, of fabric. The sleeve 7 serves to improve the appearance of the joint cuff and at the same time to protect the cushion layer 6.

Figure 1:
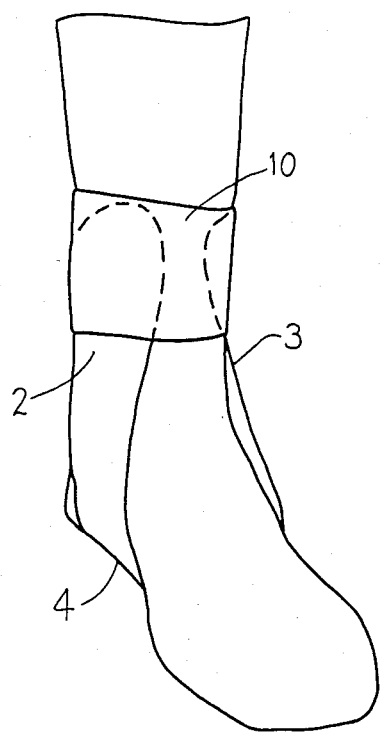
FIG. 1 is a perspective view of a joint cuff which embodies the invention and is secured on a foot.

FIG. 1 illustrates the joint cuff 1 while it is being worn. The two side portions 2 and 3 are pulled up laterally over the joint and thus grip over the joint. The two portions 2 and 3 are connected with one another by the bottom portion 4. Since the joint cuff includes a thermoplastic material, it can be formed exactly to the shape of the foot in the region of the bottom portion 4 and also to the shape of the ankle joint in the region of the side portions 2 and 3. To secure the joint cuff 1 to the foot, a bandage 10 can be wound two or three times around the leg and the portions 2 and 3. Alternatively, it is also conceivable to provide an adhesive or burr lock, for example Velcro, on the outer sides of the side portions 2 and 3 and to use a cooperating adhesive band for the connection. The height of the joint cuff is chosen so that it includes, in the rear third of the longitudinal arch at the height of the ankle fork, the upper and lower ankle joints. The very good stiffness and guiding of the joint is obtained on the one hand by the bottom portion and on the other hand by the capability to precisely adjust the shape of the joint cuff to each individual wearer.

The low-temperature thermoplastic which is used preferably softens at only 55° and can then be deformed plastically. The side portions advantageously extend upwardly at the medial side to approximately 10 cm. above the inner end of the ankle bone and on the outside to approximately 11.5 cm. above the ankle bone.

When the joint cuff includes the cushion of plastic or foam and the cover or sleeve, then adjusting of the joint cuff to the particular joint is also facilitated by the plastic or foam cushion and by the sleeve.

The inventively constructed joint cuff can also be provided as an integral part of a shoe, wherein the cuff is secured at its bottom portion to the sole of the shoe. Adjusting then occurs either by heating up the entire shoe or by selective heating of the cuff, for example by means of a hot-air blower.

Although a particular preferred embodiment of the invention has been disclosed in detail for illustrative purposes, it will be recognized that variations or modifications of the disclosed apparatus, including the rearrangement of parts, lie within the scope of the present invention.

The embodiments of the invention in which an exclusive property or privilege is claimed are defined as follows:

1. A joint cuff, in particular for the support and joint guiding of an ankle joint of a user, comprising: an elongated member having two longitudinally extending side portions interconnected by a bottom portion, said two side portions having a lateral width to enable only laterally facing portions of the ankle joint to be covered thereby, both lateral edges of said bottom portion defining an angle opening in the same direction, the entirety of said bottom portion extending to one lateral side of said central longitudinal axis of said side portions, wherein said joint cuff includes a thermoplastic material which is deformable upon application of heat thereto to enable said thermoplastic material to be conformed to the ankle joint, said thermoplastic material having a stiff characteristic at ambient temperature, and said lateral width dimension of said two side portions of said joint cuff being such that the forwardly and rearwardly facing sides of the tibia remain free from coverage by said joint cuff, while said joint cuff is substantially juxtaposed against and covers the laterally facing sides thereof, so that, in use after said side portions and said bottom portion have been respectively form fitted and fitted against the laterally facing sides of the user's ankle and the bottom of the user's foot, respectively, said side portions are held against the laterally facing sides of the ankle joint by a bandage member, the user's foot having mobility to enable the toe portion of the foot to move freely up and down but the ankle joint being reinforced in the lateral directions of movement of the foot due to said stiff characteristic of said thermoplastic material at ambient temperature.

2. The joint cuff according to claim 1, wherein said joint cuff is a single part.

3. The joint cuff according to claim 1, wherein the width of said bottom portion is 3 to 5 cm.

4. The joint cuff according to claim 1, wherein the width of each of said side portions is 6 to 11 cm.

5. The joint cuff according to claim 1, wherein a cushion layer is provided on at least one side surface of a strip of said thermoplastic material in said joint cuff.

6. The joint cuff according to claim 5, wherein said cushion layer is made of a foam material.

7. The joint cuff according to claim 1, wherein said joint cuff has as an external covering sleeve made of one of leather, artificial leather and fabric.

8. The joint cuff according to claim 1, wherein said joint cuff is an integral part of a shoe.

* * * * *